US008529895B2

(12) United States Patent
Mihara et al.

(10) Patent No.: US 8,529,895 B2
(45) Date of Patent: Sep. 10, 2013

(54) METHOD FOR SUPPRESSING THE DEVELOPMENT OF GRAFT-VERSUS-HOST-DISEASE BY ADMINISTERING INTERLEUKIN 6 RECEPTOR ANTIBODIES

(75) Inventors: Masahiko Mihara, Gotenba (JP); Yoichiro Moriya, Kamakura (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 220 days.

(21) Appl. No.: 12/733,951

(22) PCT Filed: Oct. 1, 2008

(86) PCT No.: PCT/JP2008/067835
§ 371 (c)(1),
(2), (4) Date: Mar. 31, 2010

(87) PCT Pub. No.: WO2009/044774
PCT Pub. Date: Apr. 9, 2009

(65) Prior Publication Data
US 2010/0255007 A1    Oct. 7, 2010

(30) Foreign Application Priority Data

Oct. 2, 2007  (JP) ................................. 2007-258810

(51) Int. Cl.
*A61K 39/00*      (2006.01)
*A61K 39/395*    (2006.01)
*C12P 21/08*     (2006.01)
*C07K 16/00*     (2006.01)

(52) U.S. Cl.
USPC ................. 424/133.1; 424/172.1; 530/387.3; 530/389.1

(58) Field of Classification Search
None
See application file for complete search history.

(56) References Cited

U.S. PATENT DOCUMENTS

| | | | |
|---|---|---|---|
| 5,216,128 A | 6/1993 | Novick et al. | |
| 6,086,874 A | 7/2000 | Yoshida et al. | |
| 2004/0071666 A1* | 4/2004 | Ferrara et al. | 424/93.7 |
| 2005/0119305 A1* | 6/2005 | Naka et al. | 514/317 |
| 2005/0142635 A1 | 6/2005 | Tsuchiya et al. | |
| 2010/0061986 A1 | 3/2010 | Takahashi et al. | |

FOREIGN PATENT DOCUMENTS

| | | |
|---|---|---|
| EP | 2 123 302 A1 | 11/2009 |
| FR | 2694767 A | 2/1994 |
| WO | WO 92/19759 A1 | 11/1992 |
| WO | WO 95/09873 A1 | 4/1995 |
| WO | WO 96/20728 A1 | 11/1996 |
| WO | WO 2004/039826 A1 | 5/2004 |
| WO | WO 2004/096273 A1 | 11/2004 |
| WO | WO 2007/058194 A1 | 5/2007 |
| WO | WO 2008/090901 A1 | 7/2008 |

OTHER PUBLICATIONS

International Search Report mailed Dec. 9, 2008, in PCT/JP2008/067835, 3 pages.
Akira et al., "Interleukin-6 in Biology and Medicine," Adv. in Immunology, 1993, 54:1-78.
Hirano et al., "Complementary DNA for a novel human interleukin (BSF-2) that induces B lymphocytes to produce immunoglobulin," Nature, Nov. 6, 1986, 324:73-76.
Hirata et al., "Characterization of IL-6 Receptor Expression by Monoclonal and Polyclonal Antibodies," J. Immunol., Nov. 1, 1989, 143(9):2900-2906.
Huang et al., "A Monoclonal Anti-Human IL-6 Receptor Antibody Inhibits the Proliferation of Human Myeloma Cells," Hybridoma, 1993, 12(5):621-630.
Knulst et al., "Cytokine detection and modulation in acute graft vs. host disease in mice," Mediators of Inflammation, 1994, 3(1):33-40.
Lotz et al., "B cell stimulating factor 2/interleukin 6 is a costimulant for human thymocytes and T lymphocytes," J. Exp. Med., Mar. 1988, 167:1253-1258.
Marmont et al., "T-Cell Depletion of HLA-Identical Transplants in Leukemia," Blood, Oct. 15, 1991, 78(8):2120-2130.
Novick et al., "Monoclonal Antibodies to the Soluble Human IL-6 Receptor: Affinity Purification, ELISA, and Inhibition of Ligand Binding," Hybridoma, 1991, 10(1):137-146.
Taga et al., "Interleukin-6 Triggers the Association of Its Receptor with a Possible Signal Transducer, gp130," Cell, Aug. 11, 1989, 58:573-581.
Taga et al., "Receptors for B Cell Stimulatory Factor 2," J. Exp. Med., Oct. 1987, 166:967-981.
Yamasaki et al., "Cloning and Expression of the Human Interleukin-6 (BSF-2/IFNβ 2) Receptor," Science, Aug. 12, 1988, 241:825-828.
Biswas et al., "IL-6 Deficiency Allows for Enhanced Theraptueic Value After Bone Marrow Transplantation Across a Minor Histocompatibility Barrier in the Twitcher (Globoid Cell Leukodystrophy) Mouse," Journal of Neuroscience Research, 2001, 65:298-307.
Cavet et al., "Interferon-γ and interleukin-6 gene polymorphisms associate with graft-versus-host disease in HLA-matched sibling bone marrow transplantation," Blood, Sep. 1, 2001, 98(5):1594-1600.
Database WPI, Week 200755, AN 2007-572465, XP002662508, WO 2007/058194 A1 May 24, 2007, Abstract.
Ito et al., "A Pilot Randomized Trial of a Human Anti-Interleukin-6 Receptor Monoclonal Antibody in Active Crohn's Disease," Gastroenterology, Apr. 2004, 126(4):989-996.
Jacobsohn et al., "Anti-Cytokine Therapy for the Treatment of Graft-Versus-Host Disease," Current Pharmaceutical Design, 2004, 10(11):1195-1205.

* cited by examiner

*Primary Examiner* — Robert Landsman
(74) *Attorney, Agent, or Firm* — Foley & Lardner LLP (57) ABSTRACT

The present invention provides a novel therapeutic agent for graft-versus-host disease (GVHD).
A therapeutic agent for graft-versus-host disease (GVHD), which comprises an interleukin 6 (IL-6) receptor inhibitor as an active ingredient.

2 Claims, 1 Drawing Sheet

METHOD FOR SUPPRESSING THE DEVELOPMENT OF GRAFT-VERSUS-HOST-DISEASE BY ADMINISTERING INTERLEUKIN 6 RECEPTOR ANTIBODIES

CROSS-REFERENCE TO RELATED APPLICATIONS

This application is a National Stage application of PCT/JP2008-067835, filed Oct. 1, 2008, which claims priority from Japanese application JP 2007-258810, filed Oct. 2, 2007.

TECHNICAL FIELD

The present invention relates to therapeutic agents for graft-versus-host disease. More specifically, the present invention relates to therapeutic agents for graft-versus-host disease, which comprise an interleukin 6 (IL-6) receptor inhibitor as an active ingredient.

BACKGROUND ART

Although hematopoietic tumors such as leukemia are first treated by chemotherapy with anticancer agents, patients who are difficult to cure or less likely to be cured with standard chemotherapy further require transplantation of hematopoietic stem cells (e.g., peripheral blood stem cells, bone marrow cells). However, it is pointed out that transplantation of hematopoietic stem cells will cause graft-versus-host disease (GVHD).

GVHD is a generic name for diseases that are caused by the immune reaction of transferred or transplanted immunocompetent cells against host tissues. This would be mainly because immunocompetent cells (e.g., mature T cells) contained in peripheral blood to be transferred or transplanted will cause immune responses against recipient tissues. GVHD includes both acute and chronic types of diseases with symptoms such as skin symptoms, diarrhea and icterus, which can develop a severe effect leading to death in some cases.

Techniques conventionally used to suppress GVHD include those based on the use of immunosuppressive agents such as methotrexate or cyclosporin A, as well as those based on the removal of mature T cells from a group of transplant cells (graft). In the case of using methotrexate or cyclosporin A, a problem arises from their side effects on the body. Cyclosporin A is known to have a strong nephrotoxicity as a side effect, while methotrexate is known to cause bone marrow suppression as a side effect.

On the other hand, the removal of mature T cells from a group of transplant cells allows suppression of GVHD, but it has a drawback in that the antitumor effect becomes attenuated leading to, e.g., leukemia relapse (Non-patent Document 1).

Interleukin 6 (IL-6) is a cytokine called B cell stimulating factor 2 (BSF2) or interferon β2. IL-6 was discovered as a differentiation factor involved in activation of B cell lymphocytes (Non-patent Document 2), and was later revealed to be a multifunctional cytokine that influences the function of various cells (Non-patent Document 3). IL-6 has been reported to induce maturation of T lymphocyte cells (Non-patent Document 4).

IL-6 transmits its biological activity via two kinds of proteins on the cell. The first kind of protein is IL-6 receptor, which is a ligand-binding protein to which IL-6 binds; it has a molecular weight of about 80 kDa (Non-patent Documents 5 and 6). The IL-6 receptor is present in a membrane-bound form that penetrates and is expressed on the cell membrane, and also as a soluble IL-6 receptor, which mainly consists of the extracellular region of the membrane-bound form.

The other kind of protein is the membrane protein gp130, which has a molecular weight of about 130 kDa and is involved in non-ligand binding signal transduction. The biological activity of IL-6 is transmitted into the cell through formation of an IL-6/IL-6 receptor complex from IL-6 and IL-6 receptor followed by binding of the complex with gp130 (Non-patent Document 7).

IL-6 inhibitors are substances that inhibit the transmission of IL-6 biological activity. Currently, known IL-6 inhibitors include antibodies against IL-6 (anti-IL-6 antibodies), antibodies against IL-6 receptor (anti-IL-6 receptor antibodies), antibodies against gp130 (anti-gp130 antibodies), IL-6 variants, partial peptides of IL-6 or IL-6 receptor, and such.

There are several reports regarding anti-IL-6 receptor antibodies (Non-patent Documents 8 and 9, Patent Documents 1 to 3). One such report details a humanized PM-1 antibody, which is obtained by grafting the complementarity determining region (CDR) of mouse antibody PM-1 (Non-patent Document 10), which is an anti-IL-6 receptor antibody, into a human antibody (Patent Document 4).

Antibodies against IL-6 receptor are used for treatment of inflammatory diseases such as rheumatism. However, inflammatory cytokines including IL-6 form a complex network, and hence it has been unclear whether IL-6 receptor inhibitors are effective for treatment of other diseases such as graft-versus-host disease.

In fact, it has been reported that no therapeutic effect was obtained in IL-6-expressing GVHD model mice even when administered with anti-IL-6 antibody (Non-patent Document 11).

Prior-art documents relevant to the present invention will be shown below.

Non-patent Document 1: Marmont, A M. Et al., Blood (1991) 78, 2120-2123
Non-patent Document 2: Hirano, T. et al., Nature (1986) 324, 73-76
Non-patent Document 3: Akira, S. et al., Adv. in Immunology (1993) 54, 1-78
Non-patent Document 4: Lotz, M. et al., J. Exp. Med. (1988) 167, 1253-1258
Non-patent Document 5: Taga, T. et al., J. Exp. Med. (1987) 166, 967-981
Non-patent Document 6: Yamasaki, K. et al., Science (1988) 241, 825-828
Non-patent Document 7: Taga, T. et al., Cell (1989) 58, 573-581
Non-patent Document 8: Novick, D. et al., Hybridoma (1991) 10, 137-146
Non-patent Document 9: Huang, Y. W. et al., Hybridoma (1993) 12, 621-630
Non-patent Document 10: Hirata, Y. et al., J. Immunol. (1989) 143, 2900-2906
Non-patent Document 11: Knulst A. C. et al., Mediators of Inflammation (1994) 3, 33-40
Patent Document 1: International Patent Publication No. WO 95/09873
Patent Document 2: French Patent Publication No. FR 2694767
Patent Document 3: U.S. Pat. No. 5,216,128

Patent Document 4: International Patent Publication No. WO 92/19759

DISCLOSURE OF THE INVENTION

Problems to be Solved by the Invention

Detailed roles of IL-6 receptor in GVHD have remained unclear. Also, it has not been clarified as to what effect on GVHD is produced by administration of IL-6 receptor inhibitors.

The present invention has been conducted under the circumstances described above. The object of the present invention is to provide novel therapeutic agents for GVHD.

Means for Solving the Problems

As a result of extensive and intensive efforts made to achieve the above object, the inventors of the present invention have found that anti-IL-6 receptor antibody produces a remarkable therapeutic effect in GVHD model mice. This finding led to the completion of the present invention.

Namely, the present invention more specifically provides [1] to [5] shown below.
[1] A therapeutic agent for graft-versus-host disease (GVHD), which comprises an interleukin 6 (IL-6) receptor inhibitor as an active ingredient.
[2] The therapeutic agent for GVHD according to [1] above, wherein the IL-6 receptor inhibitor is a human IL-6 receptor inhibitor.
[3] The therapeutic agent for GVHD according to [1] above, wherein the IL-6 receptor inhibitor is an anti-IL-6 receptor antibody.
[4] The therapeutic agent for GVHD according to [3] above, wherein the anti-IL-6 receptor antibody is a chimeric antibody, a humanized antibody or a human antibody.
[5] The therapeutic agent for GVHD according to any one of [1] to [4] above, which is intended for treatment of GVHD following peripheral blood stem cell transplantation.
[6] A method for treating graft-versus-host disease (GVHD), which comprises administering a therapeutically effective amount of an interleukin 6 (IL-6) receptor inhibitor.

BEST MODE FOR CARRYING OUT THE INVENTION

Herein, an "IL-6 receptor inhibitor" is a substance that blocks IL-6 receptor-mediated signal transduction and inhibits the biological activity of IL-6 receptor. Such an IL-6 receptor inhibitor may be either a substance that directly inhibits the biological activity of IL-6 receptor though binding to the IL-6 receptor or a substance that indirectly inhibits the biological activity of IL-6 receptor through binding to another substance such as gp130, but it is preferably a substance that binds to IL-6 receptor and has inhibitory activity against the binding between IL-6 and IL-6 receptor.

The IL-6 receptor inhibitors of the present invention include, but are not limited to, for example, anti-IL-6 receptor antibodies, soluble IL-6 receptor variants, partial peptides of IL-6 receptor and low molecular weight compounds that show similar activities. Preferred examples of the IL-6 receptor inhibitors of the present invention include antibodies that recognize IL-6 receptor.

The source of anti-IL-6 receptor antibodies used in the present invention is not particularly restricted; however, the antibodies are preferably derived from mammals.

Anti-IL-6 receptor antibodies used in the present invention can be obtained as polyclonal or monoclonal antibodies by using known methods. In particular, the anti-IL-6 receptor antibodies used in the present invention are preferably monoclonal antibodies derived from mammals. The monoclonal antibodies derived from mammals include those produced from hybridomas and those produced using genetic engineering methods from hosts transformed with an expression vector that comprises an antibody gene. By binding to IL-6 receptor, the antibody inhibits IL-6 binding to the IL-6 receptor, and thus blocks the transmission of IL-6 biological activity into the cell.

Examples of such antibodies include MR16-1 antibody (Tamura, T. et al., Proc. Natl. Acad. Sci. USA (1993) 90, 11924-11928); PM-1 antibody (Hirata, Y. et al., J. Immunol. (1989) 143, 2900-2906); AUK12-20 antibody, AUK64-7 antibody and AUK146-15 antibody (WO 92/19759); tocilizumab; and so on. Of these, the PM-1 antibody can be exemplified as a preferred monoclonal antibody against human IL-6 receptor, and the MR16-1 antibody as a preferred monoclonal antibody against mouse IL-6 receptor.

Basically, hybridomas producing anti-IL-6 receptor monoclonal antibody can be prepared using known techniques, as follows: Specifically, such hybridomas can be prepared by using IL-6 receptor as a sensitizing antigen to carry out immunization by a conventional immunization method, fusing the obtained immune cells with a known parent cell using a conventional cell fusion method, and screening for monoclonal antibody-producing cells using a conventional screening method.

More specifically, anti-IL-6 receptor antibodies can be produced as follows: For example, human IL-6 receptor or mouse IL-6 receptor for use as a sensitizing antigen for obtaining antibodies can be obtained by using the IL-6 receptor genes and/or amino acid sequences disclosed in European Patent Publication No. EP 325474 and JP 3-155795 A, respectively.

There are two kinds of IL-6 receptor proteins: one expressed on the cell membrane and the other separated from the cell membrane (soluble IL-6 receptor) (Yasukawa, K. et al., J. Biochem. (1990) 108, 673-676). The soluble IL-6 receptor essentially consists of the extracellular region of the cell membrane-bound IL-6 receptor, and differs from the membrane-bound IL-6 receptor in that it lacks the transmembrane region or both the transmembrane and intracellular regions. Any IL-6 receptor may be employed as an IL-6 receptor protein, so long as it can be used as a sensitizing antigen for producing anti-IL-6 receptor antibody used in the present invention.

After transforming an appropriate host cell with a known expression vector system inserted with an IL-6 receptor gene sequence, the desired IL-6 receptor protein is purified from the inside of the host cell or from the culture supernatant using a known method. This purified IL-6 receptor protein may be used as a sensitizing antigen. Alternatively, a cell expressing IL-6 receptor or a fusion protein between IL-6 receptor protein and another protein may be used as a sensitizing antigen.

Mammals to be immunized with a sensitizing antigen are not particularly limited, but are preferably selected in consideration of compatibility with the parent cell used for cell fusion. Generally, rodents such as mice, rats, and hamsters are used.

Animals are immunized with a sensitizing antigen according to known methods. For example, as a general method, animals are immunized by intraperitoneal or subcutaneous injection of a sensitizing antigen. Specifically, the sensitizing antigen is preferably diluted or suspended in an appropriate amount of phosphate-buffered saline (PBS), physiological saline or such and, if desired, further mixed and emulsified with an appropriate amount of a commonly used adjuvant (e.g., Freund's complete adjuvant), and then administered to a mammal several times, every four to 21 days. In addition, an appropriate carrier may be used for immunization with a sensitizing antigen.

Following such immunization, an increased level of a desired antibody in serum is confirmed and then immune cells are obtained from the mammal for cell fusion. Preferred immune cells for cell fusion include, in particular, spleen cells.

Mammalian myeloma cells used as parent cells, i.e., as partner cells to be fused with the above immune cells, include various known cell lines, for example, P3X63Ag8.653 (Kearney, J. F. et al., J. Immunol (1979) 123, 1548-1550), P3X63Ag8U.1 (Current Topics in Microbiology and Immunology (1978) 81, 1-7), NS-1 (Kohler, G. and Milstein, C., Eur. J. Immunol. (1976) 6, 511-519), MPC-11 (Margulies, D. H. et al., Cell (1976) 8, 405-415), SP2/0 (Shulman, M. et al., Nature (1978) 276, 269-270), F0 (de St. Groth, S. F. et al., J. Immunol. Methods (1980) 35, 1-21), S194 (Trowbridge, I. S., J. Exp. Med. (1978) 148, 313-323), R210 (Galfre, G. et al., Nature (1979) 277, 131-133), and such.

Basically, cell fusion of the aforementioned immune cells and myeloma cells can be performed using known methods, for example, the method of Milstein et al. (Kohler, G. and Milstein, C., Methods Enzymol. (1981) 73, 3-46), and such.

More specifically, the aforementioned cell fusion is achieved in standard nutrient culture medium in the presence of a cell fusion enhancing agent. For example, polyethylene glycol (PEG), Sendai virus (HVJ), and such are used as fusion enhancing agents. Further, to enhance fusion efficiency, auxiliary agents such as dimethyl sulfoxide may be added depending on needs.

The ratio of immune cells to myeloma cells used is preferably, for example, 1 to 10 immune cells for each myeloma cell. The culture medium used for the aforementioned cell fusion is, for example, RPMI1640 or MEM culture medium, which is suitable for proliferation of the aforementioned myeloma cells. A standard culture medium used for culturing this type of cell can also be used. Furthermore, serum supplements such as fetal calf serum (FCS) can be used in combination.

For cell fusion, the fusion cells (hybridomas) of interest are formed by well mixing predetermined amounts of an aforementioned immune cell and myeloma cell in an aforementioned culture medium, and then adding and mixing a PEG solution (e.g., a PEG solution with a mean molecular weight of about 1,000 to 6,000) pre-heated to about 37° C. at a concentration of 30% to 60% (w/v). Then, cell fusion agents and such that are unsuitable for the growth of hybridomas can be removed by repeatedly adding an appropriate culture medium and then removing the supernatant by centrifugation.

The above hybridomas are selected by being cultured in a standard selection culture medium, for example, HAT culture medium (a culture medium containing hypoxanthine, aminopterin, and thymidine). Culture in HAT culture medium is continued for a sufficient period, generally several days to several weeks, to kill cells other than the hybridomas of interest (unfused cells). Then, a standard limited dilution method is performed to screen and clone hybridomas that produce an antibody of interest.

In addition to the methods for immunizing non-human animals with antigens for obtaining the aforementioned hybridomas, desired human antibodies with the activity of binding to a desired antigen or antigen-expressing cell can be obtained by sensitizing a human lymphocyte with a desired antigen protein or antigen-expressing cell in vitro, and fusing the sensitized B lymphocyte with a human myeloma cell (e.g., U266) (see, JP 1-59878 B). Further, a desired human antibody can be obtained by administering an antigen or antigen-expressing cell to a transgenic animal that has a repertoire of human antibody genes, and then following the aforementioned method (see, International Patent Publication Nos. WO 93/12227, WO 92/03918, WO 94/02602, WO 94/25585, WO 96/34096, and WO 96/33735).

The thus prepared hybridomas which produce monoclonal antibodies can be subcultured in a conventional culture medium and stored in liquid nitrogen for a long period.

When obtaining monoclonal antibodies from the aforementioned hybridomas, the following methods may be employed: a method where the hybridomas are cultured according to conventional methods and the antibodies are obtained as a culture supernatant; a method where the hybridomas are administered to and proliferated in a compatible mammal and the antibodies are obtained as ascites; and so on. The former method is preferred for obtaining antibodies with high purity, and the latter is preferred for large-scale antibody production.

For example, anti-IL-6 receptor antibody-producing hybridomas can be prepared by the method disclosed in JP 3-139293 A. Such hybridomas can be prepared by injecting a PM-1 antibody-producing hybridoma into the abdominal cavity of a BALB/c mouse, obtaining ascites, and then purifying PM-1 antibody from the ascites; or by culturing the hybridoma in an appropriate medium (e.g., RPMI1640 medium containing 10% fetal bovine serum and 5% BM-Condimed H1 (Boehringer Mannheim); hybridoma SFM medium (GIBCO-BRL); PFHM-II medium (GIBCO-BRL), etc.) and then obtaining PM-1 antibody from the culture supernatant.

Recombinant antibodies can be used as the monoclonal antibodies of the present invention, wherein the antibodies are produced using genetic recombination techniques by cloning an antibody gene from a hybridoma, inserting the gene into an appropriate vector, and then introducing the vector into a host (see, for example, Borrebaeck, C. A. K. and Larrick, J. W., Therapeutic Monoclonal Antibodies, published in the United Kingdom by Macmillan Publishers Ltd, 1990).

More specifically, mRNAs encoding antibody variable (V) regions are isolated from cells that produce antibodies of interest, such as hybridomas. mRNAs can be isolated by preparing total RNAs according to known methods, such as the guanidine ultracentrifugation method (Chirgwin, J. M. et al., Biochemistry (1979) 18, 5294-5299) and the AGPC method (Chomczynski, P. et al., Anal. Biochem. (1987) 162, 156-159), and preparing mRNAs using a mRNA Purification Kit (Pharmacia) and such. Alternatively, mRNAs can be directly prepared using a QuickPrep mRNA Purification Kit (Pharmacia).

cDNAs of the antibody V regions are synthesized from the obtained mRNAs using reverse transcriptase. cDNAs may be synthesized using an AMV Reverse Transcriptase First-strand cDNA Synthesis Kit and so on. Further, to synthesize and amplify the cDNAs, the 5'-RACE method (Frohman, M.

A. et al., Proc. Natl. Acad. Sci. USA (1988) 85, 8998-9002; Belyaysky, A. et al., Nucleic Acids Res. (1989) 17, 2919-2932) using a 5'-Ampli FINDER RACE Kit (Clontech) and PCR may be employed. A DNA fragment of interest is purified from the obtained PCR products and then ligated with vector DNA. Then, a recombinant vector is prepared using the above DNA and introduced into *Escherichia coli* or such, and then its colonies are selected to prepare a desired recombinant vector. The nucleotide sequence of the DNA of interest is confirmed by a known method, for example, the dideoxy method.

Once DNA encoding the V region of an antibody of interest has been obtained, the DNA is ligated with DNA that encodes a desired antibody constant region (C region), and inserted into an expression vector. Alternatively, DNA encoding an antibody V region may be inserted into an expression vector comprising DNA of an antibody C region.

To produce an antibody to be used in the present invention, as described below, an antibody gene is inserted into an expression vector such that it is expressed under the control of an expression regulating region, for example, an enhancer and promoter. Then, the antibody can be expressed by transforming a host cell with this expression vector.

In the present invention, to reduce heteroantigenicity against humans and such, artificially modified genetic recombinant antibodies, for example, chimeric antibodies or humanized antibodies, can be used. These modified antibodies can be prepared using known methods.

A chimeric antibody can be obtained by ligating DNA encoding an antibody V region, obtained as above, with DNA encoding a human antibody C region, then inserting the DNA into an expression vector and introducing it into a host for production (see, European Patent Publication No. EP 125023; International Patent Publication No. WO 92/19759). This known method can be used to obtain chimeric antibodies useful for the present invention.

Humanized antibodies are also referred to as reshaped human antibodies, and are antibodies wherein the complementarity determining regions (CDRs) of an antibody from a non-human mammal (e.g., a mouse antibody) are grafted into the CDRs of human antibodies. General methods for this gene recombination are also known (see, European Patent Publication No. EP 125023, International Patent Publication No. WO 92/19759).

More specifically, DNA sequences designed such that the CDRs of a mouse antibody are ligated with the framework regions (FRs) of a human antibody are synthesized by PCR from several oligonucleotides produced to contain overlapping portions at their termini. The obtained DNA is ligated with human antibody C region-encoding DNA and then inserted into an expression vector. The expression vector is introduced into a host to produce the humanized antibody (see, European Patent Publication No. EP 239400, International Patent Publication No. WO 92/19759).

The human antibody FRs to be ligated via the CDRs are selected so that the CDRs form suitable antigen binding sites. Amino acid(s) within the FRs of the antibody variable regions may be substituted as necessary so that the CDRs of the reshaped human antibody form appropriate antigen binding sites (Sato, K. et al., Cancer Res. (1993) 53, 851-856).

Human antibody C regions are generally used for chimeric and humanized antibodies. Examples of human antibody heavy chain C regions include $C\gamma$, $C\alpha$, $C\mu$, $C\delta$ and $C\epsilon$, and for example, $C\gamma1$, $C\gamma2$, $C\gamma3$ or $C\gamma4$ may be used. Examples of human antibody light chain C regions include $\kappa$ or $\lambda$. Furthermore, to improve the stability of the antibodies or their production, the human antibody C regions may be modified.

Chimeric antibodies consist of the variable regions of an antibody derived from a non-human mammal and the constant regions of an antibody derived from a human; humanized antibodies consist of the CDRs of an antibody derived from a non-human mammal and the framework regions and constant regions derived from a human antibody. These have reduced antigenicity in the human body, and are thus useful as antibodies for use in the present invention.

Preferred specific examples of humanized antibodies for use in the present invention include humanized PM-1 antibody (tocilizumab; see, International Patent Publication No. WO 92/19759). Alternatively, modified forms of the humanized PM-1 antibody are also possible, which are designed to comprise substitutions, deletions, additions or other modifications in the amino acid sequence of the humanized PM-1 antibody.

Furthermore, in addition to the aforementioned methods for obtaining human antibodies, techniques for obtaining human antibodies by panning using a human antibody library are also known. For example, the variable regions of human antibodies can be expressed on phage surfaces as single chain antibodies (scFv) by using the phage display method to thereby select antigen-binding phages. By analyzing the genes of the selected phages, DNA sequences encoding the human antibody variable regions that bind to the antigen can be determined. Once the DNA sequence of scFv that binds to the antigen is revealed, an appropriate expression vector comprising the sequence can be constructed to obtain a human antibody. These methods are already known, and the publications of WO 92/01047, WO 92/20791, WO93/06213, WO 93/11236, WO 93/19172, WO 95/01438, and WO 95/15388 can be used as reference.

The antibody genes constructed above can be expressed according to conventional methods. When a mammalian cell is used, the antibody gene can be expressed using DNA in which the antibody gene to be expressed is operably linked to a useful commonly used promoter and a poly A signal downstream of the antibody gene, or using a vector comprising the DNA. Examples of a promoter/enhancer include the human cytomegalovirus immediate early promoter/enhancer.

Furthermore, other promoters/enhancers that can be used for expressing the antibodies for use in the present invention include viral promoters/enhancers from retrovirus, polyoma virus, adenovirus, simian virus 40 (SV40), and such; and also include mammalian cell-derived promoters/enhancers such as human elongation factor $1\alpha$ (HEF$1\alpha$).

For example, when the SV40 promoter/enhancer is used, the expression can be easily performed according to the method of Mulligan et al. (Mulligan, R. C. et al., Nature (1979) 277, 108-114). Alternatively, in the case of using the HEF$1\alpha$ promoter/enhancer, the method of Mizushima et al. (Mizushima, S. and Nagata S., Nucleic Acids Res. (1990) 18, 5322) can be used.

Production systems using prokaryotic host cells include those using bacterial cells. Known bacterial cells include *E. coli* and *Bacillus subtilis*.

When *E. coli* is used, an antibody gene can be expressed by operably liking a conventional useful promoter, a signal sequence for antibody secretion, and the antibody gene to be expressed. Examples of such a promoter include lacZ promoter, araB promoter and such. When the lacZ promoter is used, genes can be expressed according to the method of Ward et al. (Ward, E. S. et al., Nature (1989) 341, 544-546; Ward, E. S. et al., FASEB J. (1992) 6, 2422-2427); and the araB promoter may be used according to the method of Better et al. (Better, M. et al., Science (1988) 240, 1041-1043).

When the antibody is produced into the periplasm of *E. coli*, the pel B signal sequence (Lei, S. P. et al., J. Bacteriol. (1987) 169, 4379-4383) may be used as a signal sequence for antibody secretion. The antibodies produced into the periplasm are isolated and appropriately refolded before use (see, for example, WO 96/30394).

As the replication origin, those derived from SV40, polyoma virus, adenovirus, bovine papilloma virus (BPV) and such may be used. In addition, to enhance the gene copy number in a host cell system, the expression vector may comprise the aminoglycoside phosphotransferase (APH) gene, thymidine kinase (TK) gene, *E. coli* xanthine-guanine phosphoribosyltransferase (Ecogpt) gene, dihydrofolate reductase (dhfr) gene, or such as a selection marker.

Any production system may be used to prepare the antibodies for use in the present invention. The production systems for antibody preparation include in vitro and in vivo production systems. In vitro production systems include those using eukaryotic cells or prokaryotic cells.

Production systems using eukaryotic host cells include those using animal cells, plant cells, or fungal cells. Such animal cells include (1) mammalian cells, for example, CHO, COS, myeloma, baby hamster kidney (BHK), HeLa, Vero, and such; (2) amphibian cells, for example, *Xenopus oocyte*; and (3) insect cells, for example, sf9, sf21, Tn5, and such. Known plant cells include those derived from *Nicotiana tabacum*, which may be cultured as a callus. Known fungal cells include yeasts such as *Saccharomyces* (e.g., *S. cerevisiae*), mold fungi such as *Aspergillus* (e.g., *A. niger*), and such.

Antibodies can be obtained by using transformation to introduce an antibody gene of interest into these cells, and then culturing the transformed cells in vitro. Cultures are conducted according to known methods. For example, DMEM, MEM, RPMI1640, IMDM may be used as the culture medium, and serum supplements such as FCS may be used in combination. Further, the cells introduced with the antibody gene may be transferred into the abdominal cavity or such of an animal to produce the antibodies in vivo.

On the other hand, in vivo production systems include those using animals or plants. Production systems using animals include those that use mammals or insects.

Mammals that can be used include goats, pigs, sheep, mice, bovines and such (Vicki Glaser, SPECTRUM Biotechnology Applications, 1993). Further, insects that can be used include silkworms. When using plants, tobacco may be used, for example.

An antibody gene is introduced into these animals or plants, and the antibody is produced in the body of the animals or plants and then recovered. For example, an antibody gene can be prepared as a fusion gene by being inserted into the middle of a gene encoding a protein such as goat β casein, which is uniquely produced into milk. DNA fragments comprising the fusion gene, which includes the antibody gene, are injected into goat embryos, and the embryos are introduced into female goats. The desired antibody is obtained from milk produced by the transgenic animals born to the goats that received the embryos, or produced from progenies of these animals. The transgenic goats can be given hormones to increase the volume of milk containing the desired antibody that they produce (Ebert, K. M. et al., Bio/Technology (1994) 12, 699-702).

When silkworms are used, the silkworms are infected with baculovirus inserted with a desired antibody gene, and the desired antibody is obtained from the body fluids of these silkworms (Maeda, S. et al., Nature (1985) 315, 592-594). Moreover, when tobacco is used, a desired antibody gene is inserted into a plant expression vector (e.g., pMON530) and the vector is introduced into bacterial cells such as *Agrobacterium tumefaciens*. These bacterial cells are used to infect tobacco (e.g., *Nicotiana tabacum*) such that desired antibodies can be obtained from the leaves of this tobacco (Julian, K. -C. Ma et al., Eur. J. Immunol. (1994) 24, 131-138).

When producing antibodies using in vitro or in vivo production systems, as described above, DNAs encoding an antibody heavy chain (H chain) and light chain (L chain) may be inserted into separate expression vectors and co-transformed into a host. Alternatively, DNAs encoding the H and L chains may be inserted into a single expression vector for transforming a host (see International Patent Publication No. WO 94/11523).

The antibodies used in the present invention may be antibody fragments or modified products thereof, so long as they can be suitably used in the present invention. For example, antibody fragments include Fab, F(ab')2, Fv, and single chain Fv (scFv), in which the Fvs of the H and L chains are linked via an appropriate linker.

Specifically, antibody fragments are produced by treating antibodies with enzymes, for example, papain or pepsin, or alternatively, genes encoding these fragments are constructed, introduced into expression vectors, and then expressed in appropriate host cells (see, for example, Co, M. S. et al., J. Immunol. (1994) 152, 2968-2976; Better, M. & Horwitz, A. H., Methods in Enzymology (1989) 178, 476-496; Plueckthun, A. & Skerra, A., Methods in Enzymology (1989) 178, 497-515; Lamoyi, E., Methods in Enzymology (1989) 121, 652-663; Rousseaux, J. et al., Methods in Enzymology (1989) 121, 663-666; Bird, R. E. et al., TIBTECH (1991) 9, 132-137).

scFv can be obtained by linking the H-chain V region and the L-chain V region of an antibody. In the scFv, the H-chain V region and the L-chain V region are linked via a linker, preferably via a peptide linker (Huston, J. S. et al., Proc. Natl. Acad. Sci. USA (1988) 85, 5879-5883). The V regions of the H and L chains in scFv may be derived from any of the antibodies described above. Peptide linkers for linking the V regions include, for example, arbitrary single chain peptides consisting of 12 to 19 amino acid residues.

scFv-encoding DNA can be obtained by using DNA encoding the above antibody H chain or H-chain V region and DNA encoding the above antibody L chain or L-chain V region as templates in PCR to amplify a DNA portion that encodes a desired amino acid sequence in the template sequence with primers that define the termini of the portion, and then further amplifying the amplified DNA portion with DNA that encodes a peptide linker portion and primer pairs that link both ends of the linker to the H and L chains, respectively.

Once scFv-encoding DNA has been obtained, an expression vector comprising the DNA and a host transformed with the vector can be obtained according to conventional methods. In addition, scFv can be obtained according to conventional methods using the host.

These antibody fragments can be produced from hosts by obtaining and expressing their genes, as described above. Herein, the term "antibody" encompasses such antibody fragments.

Antibodies bound to various molecules, such as polyethylene glycol (PEG), may also be used as modified antibodies. Herein, the term "antibody" encompasses such modified antibodies. These modified antibodies can be obtained by chemically modifying the obtained antibodies. Such methods are already established in the art.

Antibodies produced and expressed as above can be isolated from the inside or outside of the cells or from the hosts, and then purified to homogeneity. The antibodies for use in the present invention can be isolated and/or purified using affinity chromatography. Columns to be used for affinity chromatography include, for example, protein A columns and protein G columns. Carriers used for protein A columns include, for example, HyperD, POROS, Sepharose FF and such. In addition to the above, other methods commonly used for isolation and/or purification of proteins may be used, and are not limited in any way.

For example, the antibodies used in the present invention may be isolated and/or purified by appropriately selecting and combining chromatographies in addition to affinity chromatography, filters, ultrafiltration, salting-out, dialysis, and such. Chromatographies include, for example, ion-exchange chromatography, hydrophobic chromatography, gel filtration, and such. These chromatographies can be applied to high performance liquid chromatography (HPLC). Alternatively, reverse phase HPLC may be used.

The concentration of the antibodies obtained as above can be determined by absorbance measurement, ELISA, or such. Specifically, absorbance is determined by appropriately diluting the antibody solution with PBS(−), measuring the absorbance at 280 nm, and calculating the concentration (1.35 OD=1 mg/ml). Alternatively, when using ELISA, the measurement can be performed as follows: Specifically, goat anti-human IgG (TAG) diluted to 1 µg/ml with 0.1 M bicarbonate buffer (pH 9.6) is added at 100 µl per well in a 96-well plate (Nunc) and incubated overnight at 4° C. to immobilize the antibody. After blocking, an appropriately diluted antibody of the present invention or an appropriately diluted sample comprising the antibody, or human IgG (CAPPEL) as a standard is added in 100 µl volumes and incubated for one hour at room temperature.

After washing, 5,000× diluted alkaline phosphatase-labeled anti-human IgG (BIO SOURCE) is added in 100 µl volumes and incubated for one hour at room temperature. After another wash, a substrate solution is added and incubated, and the absorbance at 405 nm is measured using a Microplate Reader Model 3550 (Bio-Rad) to calculate the concentration of the antibody of interest.

Partial peptides of IL-6 receptor are peptides that comprise part or all of the amino acid sequence of the region of the IL-6 receptor amino acid sequence that is involved in the binding between IL-6 and IL-6 receptor. Such peptides usually comprise 10 to 80, preferably 20 to 50, more preferably 20 to 40 amino acid residues.

IL-6 receptor partial peptides can be produced according to generally known methods, for example, genetic engineering techniques or peptide synthesis methods, by specifying the region of the IL-6 receptor amino acid sequence that is involved in the binding between IL-6 and IL-6 receptor, and using a portion or entirety of the amino acid sequence of the specified region.

When preparing an IL-6 receptor partial peptide using genetic engineering methods, a DNA sequence encoding the desired peptide is inserted into an expression vector, and then the peptide can be obtained by applying the aforementioned methods for expressing, producing and purifying recombinant antibodies.

When producing an IL-6 receptor partial peptide by using peptide synthesis methods, generally used peptide synthesis methods, for example, solid phase synthesis methods or liquid phase synthesis methods, may be used.

Specifically, the peptides can be synthesized according to the method described in "Continuation of Development of Pharmaceuticals, Vol. 14, Peptide Synthesis (in Japanese) (ed. Haruaki Yajima, 1991, Hirokawa Shoten)". As a solid phase synthesis method, for example, the following method can be employed: the amino acid corresponding to the C terminus of the peptide to be synthesized is bound to a support that is insoluble in organic solvents, then the peptide strand is elongated by alternately repeating (1) the reaction of condensing amino acids, whose α-amino groups and branch chain functional groups are protected with appropriate protecting groups, one at a time in a C- to N-terminal direction; and (2) the reaction of removing the protecting groups from the α-amino groups of the resin-bound amino acids or peptides. Solid phase peptide synthesis is broadly classified into the Boc method and the Fmoc method, depending on the type of protecting groups used.

After synthesizing a peptide of interest as above, deprotection reactions are carried out, then the peptide strand is cleaved from its support. For the cleavage reaction of the peptide strand, hydrogen fluoride or trifluoromethane sulfonic acid is generally used in the Boc method, and TFA is generally used in the Fmoc method. In the Boc method, for example, the above-mentioned protected peptide resin is treated with hydrogen fluoride in the presence of anisole. Then, the peptide is recovered by removing the protecting groups and cleaving the peptide from its support. By freeze-drying the recovered peptide, a crude peptide can be obtained. In the Fmoc method, on the other hand, the deprotection reaction and the reaction to cleave the peptide strand from the support can be performed in TFA using a method similar to those described above, for example.

Obtained crude peptides can be separated and/or purified by being applied to HPLC. Elution may be performed under optimum conditions using a water-acetonitrile solvent system, which is generally used for protein purification. Fractions corresponding to the peaks of the obtained chromatographic profile are collected and freeze-dried. The peptide fractions thus purified are identified by molecular weight analysis via mass spectrometry, amino acid composition analysis, amino acid sequence analysis, or such.

The therapeutic agents for GVHD of the present invention can be used in treating and/or preventing GVHD. The therapeutic agents for GVHD of the present invention also include prophylactic agents for GVHD which suppress the development of GVHD. Thus, the phrase "therapeutic (agent) for GVHD" as used herein is intended to mean suppressing GVHD, reducing the % occurrence of GVHD, treating GVHD, ameliorating the symptoms of GVHD, etc.

Any type of GVHD can be treated by the therapeutic agents of the present invention. GVHD that can be treated by the therapeutic agents of the present invention includes acute GVHD and chronic GVHD. The therapeutic agents for GVHD of the present invention are particularly effective against GVHD following hematopoietic stem cell transplantation, such as GVHD following peripheral blood stem cell transplantation (e.g., allogeneic peripheral blood stem cell transplantation) or GVHD following bone marrow transplantation (e.g., allogeneic bone marrow transplantation).

IL-6 receptor inhibitors used in the present invention can be evaluated for their effect as therapeutic agents for GVHD, for example but not limited to, by using their inhibitory activity against signal transduction as an index. The inhibitory activity of IL-6 receptor inhibitors against signal transduction can be evaluated by conventional methods. Specifically, IL-6 is added to cultures of IL-6-dependent human myeloma cell lines (S6B45 and KPMM2), human Lennert T lymphoma cell line KT3, or IL-6-dependent cell line MH60.BSF2; and the $^3$H-thymidine uptake by the IL-6-dependent cells is measured in the presence of an IL-6 receptor inhibitor. Alternatively, IL-6 receptor-expressing U266 cells are cultured, and $^{125}$I-labeled IL-6 and an IL-6 receptor inhibitor are added to the culture at the same time; and then $^{125}$I-labeled IL-6 bound to the IL-6 receptor-expressing cells is quantified. In addition to the IL-6 receptor inhibitor group, a negative control group that contains no IL-6 receptor inhibitor is included in the assay system described above. The activity of the IL-6 receptor inhibitor to inhibit IL-6 receptor can be evaluated by comparing the results of both groups.

Subjects to be administered with the therapeutic agents for GVHD of the present invention are mammals. The mammals are preferably humans.

The therapeutic agents for GVHD of the present invention can be administered as pharmaceuticals, and may be administered systemically or locally via oral or parenteral administration. For example, intravenous injections such as drip infusions, intramuscular injections, intraperitoneal injections, subcutaneous injections, suppositories, enemas, oral enteric tablets, or the like can be selected. Appropriate administration methods can be selected depending on a patient's age and symptoms. The effective dose per administration is not limited in any way, but is selected from the range of 0.01 to 100 mg/kg body weight. Alternatively, the dose may be selected from the range of 1 to 1000 mg/patient, preferably from the range of 5 to 50 mg/patient. By way of specific example, a preferred dose and administration method are as follows: For example, when anti-IL-6 receptor antibody is used, a dose of 0.5 to 40 mg/kg body weight/month (four weeks), preferably 1 to 20 mg/kg body weight/month is administered via an intravenous injection such as a drip infusion, subcutaneous injection, intramuscular injection or such, once to several times a month, for example, twice a week, once a week, once every two weeks, or once every four weeks. The administration schedule may be adjusted by, for example, extending the administration interval of twice a week or once a week to once every two weeks, once every three weeks, or once every four weeks, while monitoring the patient's condition and changes in the blood test values.

As described later in the Example section, the therapeutic agents for GVHD of the present invention were able to remarkably suppress the development of GVHD when administered to recipients before and after hematopoietic stem cell transplantation. Thus, the therapeutic agents for GVHD of the present invention are preferably administered before hematopoietic stem cell transplantation and further administered after the transplantation depending on the condition of GVHD.

The therapeutic agents for GVHD of the present invention may be administered in combination with at least one known therapeutic agent or method for GVHD. For example, the therapeutic agents of the present invention may be administered simultaneously or sequentially with an immunosuppressive agent(s) (e.g., cyclosporin, tacrolimus, methotrexate) used for prevention of GVHD. Moreover, the therapeutic agents of the present invention may be combined with removal of mature T cells from a group of transplant cells (graft).

The therapeutic agents for GVHD of the present invention may contain pharmaceutically acceptable carriers, such as preservatives and stabilizers. "Pharmaceutically acceptable carriers" refer to materials that can be co-administered with the above agents. Such pharmaceutically acceptable materials include, for example, sterile water, physiological saline, stabilizers, excipients, buffers, preservatives, detergents, chelating agents (e.g., EDTA), and binders.

In the present invention, detergents include non-ionic detergents, and typical examples of such include sorbitan fatty acid esters such as sorbitan monocaprylate, sorbitan monolaurate, and sorbitan monopalmitate; glycerin fatty acid esters such as glycerin monocaprylate, glycerin monomyristate and glycerin monostearate; polyglycerin fatty acid esters such as decaglyceryl monostearate, decaglyceryl distearate, and decaglyceryl monolinoleate; polyoxyethylene sorbitan fatty acid esters such as polyoxyethylene sorbitan monolaurate, polyoxyethylene sorbitan monooleate, polyoxyethylene sorbitan monostearate, polyoxyethylene sorbitan monopalmitate, polyoxyethylene sorbitan trioleate, and polyoxyethylene sorbitan tristearate; polyoxyethylene sorbit fatty acid esters such as polyoxyethylene sorbit tetrastearate and polyoxyethylene sorbit tetraoleate; polyoxyethylene glycerin fatty acid esters such as polyoxyethylene glyceryl monostearate; polyethylene glycol fatty acid esters such as polyethylene glycol distearate; polyoxyethylene alkyl ethers such as polyoxyethylene lauryl ether; polyoxyethylene polyoxypropylene alkyl ethers such as polyoxyethylene polyoxypropylene glycol, polyoxyethylene polyoxypropylene propyl ether, and polyoxyethylene polyoxypropylene cetyl ether; polyoxyethylene alkyl phenyl ethers such as polyoxyethylene nonylphenyl ether; polyoxyethylene hardened castor oils such as polyoxyethylene castor oil and polyoxyethylene hardened castor oil (polyoxyethylene hydrogenated castor oil); polyoxyethylene beeswax derivatives such as polyoxyethylene sorbit beeswax; polyoxyethylene lanolin derivatives such as polyoxyethylene lanolin; and polyoxyethylene fatty acid amides and such with an HLB of 6 to 18, such as polyoxyethylene stearic acid amide.

Detergents also include anionic detergents, and typical examples of such include, for example, alkyl sulfates having an alkyl group with 10 to 18 carbon atoms, such as sodium cetyl sulfate, sodium lauryl sulfate, and sodium oleyl sulfate; polyoxyethylene alkyl ether sulfates in which the alkyl group has 10 to 18 carbon atoms and the average molar number of added ethylene oxide is 2 to 4, such as sodium polyoxyethylene lauryl sulfate; alkyl sulfosuccinate ester salts having an alkyl group with 8 to 18 carbon atoms, such as sodium lauryl sulfosuccinate ester; natural detergents, for example, lecithin; glycerophospholipids; sphingo-phospholipids such as sphingomyelin; and sucrose fatty acid esters in which the fatty acids have 12 to 18 carbon atoms.

One or more of the detergents described above can be combined and added to the agents of the present invention. Detergents that are preferably used in the preparations of the present invention include polyoxyethylene sorbitan fatty acid esters, such as polysorbates 20, 40, 60 and 80. Polysorbates 20 and 80 are particularly preferred. Polyoxyethylene polyoxypropylene glycols, such as poloxamer (e.g., Pluronic F-68®), are also preferred.

The amount of detergent added varies depending on the type of detergent used. When polysorbate 20 or 80 is used, the amount is in general in the range of 0.001 to 100 mg/ml, preferably in the range of 0.003 to 50 mg/ml, more preferably in the range of 0.005 to 2 mg/ml.

In the present invention, buffers include phosphate or citrate buffer, acetic acid, malic acid, tartaric acid, succinic acid, lactic acid, potassium phosphate, gluconic acid, capric acid, deoxycholic acid, salicylic acid, triethanolamine, fumaric acid, and other organic acids; as well as carbonate buffer, Tris buffer, histidine buffer, and imidazole buffer.

Liquid preparations may be formulated by dissolving the agents in aqueous buffers known in the field of liquid preparations. The buffer concentration is in general in the range of 1 to 500 mM, preferably in the range of 5 to 100 mM, more preferably in the range of 10 to 20 mM.

The therapeutic agents of the present invention may also comprise other low-molecular-weight polypeptides; proteins such as serum albumin, gelatin, and immunoglobulin; amino acids; sugars and carbohydrates such as polysaccharides and monosaccharides, sugar alcohols, and such.

Herein, amino acids include basic amino acids, for example, arginine, lysine, histidine, and ornithine, and inorganic salts of these amino acids (preferably hydrochloride salts, and phosphate salts, namely phosphate amino acids). When free amino acids are used, the pH is adjusted to a preferred value by adding appropriate physiologically acceptable buffering substances, for example, inorganic acids, in particular hydrochloric acid, phosphoric acid, sulfuric acid, acetic acid, and formic acid, and salts thereof. In this case, the use of phosphate is particularly beneficial because it gives quite stable freeze-dried products. Phosphate is particularly advantageous when preparations do not substantially contain organic acids, such as malic acid, tartaric acid, citric acid, succinic acid, and fumaric acid, or do not contain corresponding anions (e.g., malate ion, tartrate ion, citrate ion, succinate ion, fumarate ion). Preferred amino acids are arginine, lysine, histidine, and ornithine. It is also possible to use acidic amino acids such as glutamic acid and aspartic acid, and salts thereof (preferably sodium salts); neutral amino acids such as isoleucine, leucine, glycine, serine, threonine, valine, methionine, cysteine, and alanine; or aromatic amino acids such as phenylalanine, tyrosine, tryptophan, and its derivative, N-acetyl tryptophan.

Herein, sugars and carbohydrates such as polysaccharides and monosaccharides include, for example, dextran, glucose, fructose, lactose, xylose, mannose, maltose, sucrose, trehalose, and raffinose.

Herein, sugar alcohols include, for example, mannitol, sorbitol, and inositol.

When the agents of the present invention are prepared as aqueous solutions for injection, the agents may be mixed with, for example, physiological saline, and/or isotonic solution containing glucose or other auxiliary agents (e.g., D-sorbitol, D-mannose, D-mannitol, sodium chloride). The aqueous solutions may be used in combination with appropriate solubilizers such as alcohols (e.g., ethanol), polyalcohols (e.g., propylene glycol, PEG), or non-ionic detergents (e.g., polysorbate 80, HCO-50).

The agents may further comprise, if required, diluents, solubilizers, pH adjusters, soothing agents, sulfur-containing reducing agents, antioxidants, and such.

Herein, the sulfur-containing reducing agents include, for example, compounds comprising sulfhydryl groups, such as N-acetylcysteine, N-acetylhomocysteine, thioctic acid, thiodiglycol, thioethanolamine, thioglycerol, thiosorbitol, thioglycolic acid and salts thereof, sodium thiosulfate, glutathione, and thioalkanoic acids having 1 to 7 carbon atoms.

Moreover, the antioxidants in the present invention include, for example, erythorbic acid, dibutylhydroxy toluene, butylhydroxy anisole, α-tocopherol, tocopherol acetate, L-ascorbic acid and salts thereof, L-ascorbic acid palmitate, L-ascorbic acid stearate, sodium hydrogen sulfite, sodium sulfite, triamyl gallate, propyl gallate, and chelating agents such as disodium ethylenediamine tetraacetate (EDTA), sodium pyrophosphate, and sodium metaphosphate.

If required, the agents may be encapsulated in microcapsules (microcapsules of hydroxymethylcellulose, gelatin, poly[methylmethacrylic acid], etc.) or prepared as colloidal drug delivery systems (e.g., liposome, albumin microspheres, microemulsion, nano-particles, nano-capsules) (see "Remington's Pharmaceutical Science 16$^{th}$ edition", Oslo Ed., 1980, and the like). Furthermore, methods for preparing agents as sustained-release agents are also known, and are applicable to the present invention (Langer et al., J. Biomed. Mater. Res. 1981, 15: 167-277; Langer, Chem. Tech. 1982, 12: 98-105; U.S. Pat. No. 3,773,919; European Patent Publication No. (EP) 58,481; Sidman et al., Biopolymers 1983, 22: 547-556; and EP 133,988).

Pharmaceutically acceptable carriers used are appropriately selected from those described above or combined depending on the type of dosage form, but are not limited thereto.

The present invention relates to a method for treating and/or preventing GVHD in a subject, which comprises the step of administering an IL-6 receptor inhibitor to a subject developing GVHD or a subject at risk of developing GVHD.

Herein, the "subject" refers to an organism or an organism body part to be administered with the therapeutic agents for GVHD of the present invention. Such an organism includes animals (for example, human, domestic animal species, and wild animals) but is not particularly limited.

Herein, "administration" includes oral and parenteral administration. Oral administration includes, for example, administration of oral agents. Such oral agents include, for example, granules, powders, tablets, capsules, solutions, emulsions, and suspensions.

Parenteral administration includes, for example, administration of injections. Such injections include, for example, subcutaneous injections, intramuscular injections, intravenous injections and intraperitoneal injections. Meanwhile, the effects of the method of the present invention can be achieved by introducing genes comprising oligonucleotides to be administered to living bodies using gene therapy techniques. Alternatively, the agents of the present invention may be administered locally to the intended areas of treatment. For example, the agents can be administered by local injection during surgery, use of catheters, or targeted gene delivery of DNAs encoding the peptides of the present invention.

All prior-art documents cited herein are incorporated herein by reference.

The present invention will be further described in more detail by way of the following example, which is not intended to limit the invention. Various changes and modifications can be made by those skilled in the art, and these changes and modifications also fall within the present invention.

EXAMPLES

Example 1

Effect of IL-6 Receptor Antibody on GVHD

Test Method

Spleen cells ($6 \times 10^7$ cells/mouse) obtained from female C57BL/6J donor mice at 8 weeks of age (Charles River Japan, Inc.) were transferred to female B6D2F1/Crlj recipient mice at 8 weeks of age (Charles River Japan, Inc.) via the tail vein to induce GVHD.

The recipient mice were divided into two groups, one of which was administered with anti-mouse IL-6 receptor antibody MR16-1 (Chugai Pharmaceutical Co., Ltd., Japan) at 4 mg/mouse via the tail vein at 1 day before spleen cell transfer and then at 0.5 mg/mouse via the intraperitoneal route four times every 7 days. The control group was administered with phosphate-buffered saline (PBS; SIGMA-ALDRICH Inc.) (10 animals for each group). After spleen cell transfer, the mice were measured for their body weight three times a week to evaluate the development of GVHD based on their body weight.

Results

Figure 1:
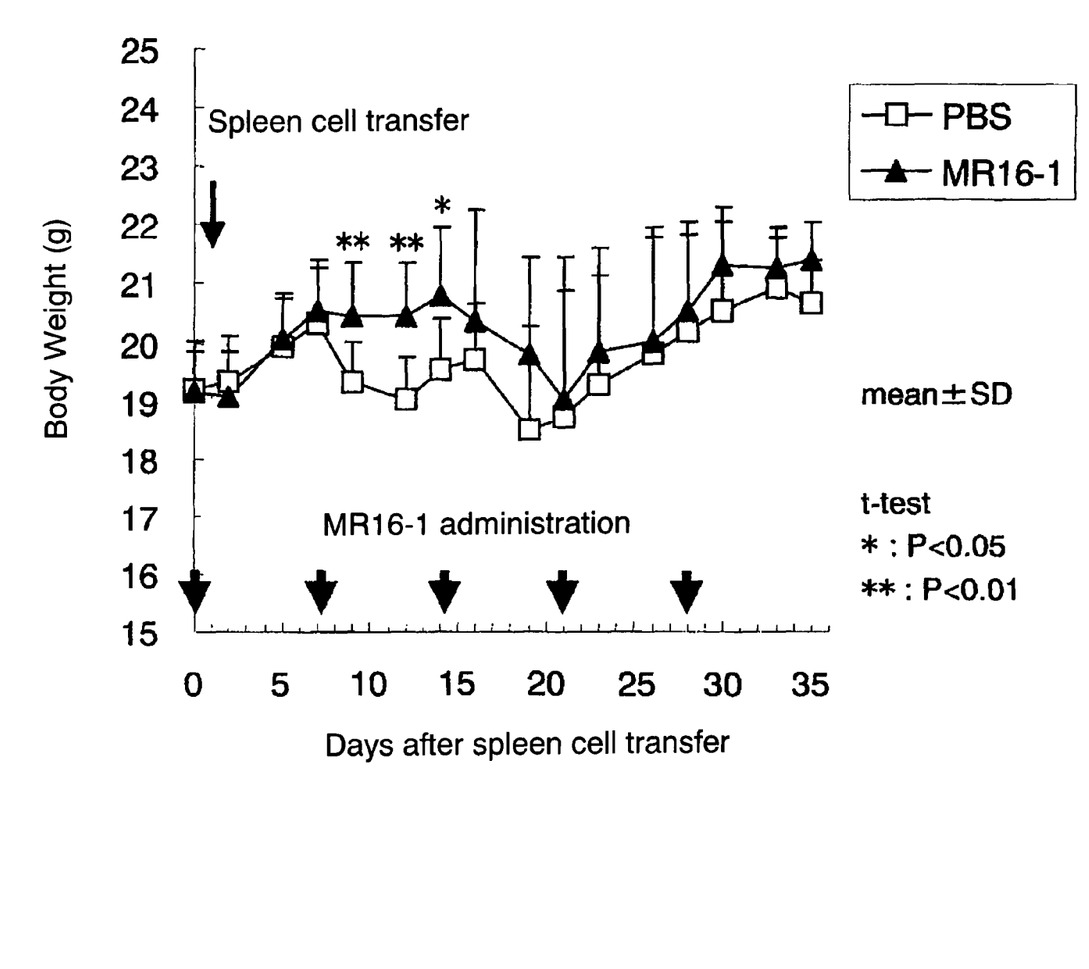
FIG. 1 is a graph showing the time course of changes in the body weight of GVHD-induced mice in the anti-IL-6 receptor antibody group and the control group.

The results obtained are shown in FIG. 1. The control group showed a biphasic decrease in the body weight. Namely, the body weight was decreased on days 9 to 14 after spleen cell transplantation and then recovered on day 16, but decreased again on days 19 to 21 and then substantially recovered on day 33. In contrast, the MR16-1-receiving group showed no decrease in the body weight on days 9 to 14. Namely, these results suggest that anti-IL-6 receptor antibody suppresses the development of GVHD.

The invention claimed is:

1. A method for suppressing the development of graft-versus-host disease (GVHD), which comprises administering to a subject in need thereof a therapeutically effective amount of an interleukin 6 (IL-6) receptor antibody.

2. The method of claim 1, wherein the anti-IL-6 receptor antibody is a chimeric antibody, a humanized antibody or a human antibody.

* * * * *